United States Patent [19]
Greene

[11] Patent Number: 5,815,254
[45] Date of Patent: Sep. 29, 1998

[54] TRANSMITTANCE AND REFLECTANCE MEASURING SPECTROPHOTOMETER HAVING DUAL USE LIGHT CHANNELS

[75] Inventor: Gary R. Greene, Penfield, N.Y.

[73] Assignee: Spectronic Instruments, Inc., Rochester, N.Y.

[21] Appl. No.: 728,296

[22] Filed: Oct. 8, 1996

[51] Int. Cl.$^6$ ............................................... G01N 21/17
[52] U.S. Cl. ............................................ 356/73; 356/435
[58] Field of Search ............................... 356/73, 153, 435

[56] References Cited

U.S. PATENT DOCUMENTS

| | | | |
|---|---|---|---|
| 4,171,909 | 10/1979 | Kramer et al. | 356/73 |
| 4,786,169 | 11/1988 | Brierley et al. | 356/73 |
| 4,853,542 | 8/1989 | Milosevic et al. | 356/446 |
| 4,937,637 | 6/1990 | Magistro | 356/73 |
| 5,268,748 | 12/1993 | Van Hijningen et al. | 356/435 |

*Primary Examiner*—Frank G. Font
*Assistant Examiner*—Zandra V. Smith
*Attorney, Agent, or Firm*—Harris, Beach & Wilcox

[57] ABSTRACT

An apparatus and method are provided for selectively measuring color values of a transmittance sample in a transmittance mode and a reflectance sample in a reflectance mode. The spectrophotometer includes two light channels, a first light channel from a light source to a first detector and a second light channel from the same light source to a second detector. The light channels conduct the light through the spectrophotometer. The spectrophotometer includes appropriate circuitry to compare the light striking the first and second detectors to determine the color value of a sample. A transmittance cell is located in the first light channel for selectively receiving a transmittance sample. When a sample is present, light passing through the transmittance sample is altered because the sample selectively absorbs some of the wavelengths of light. The spectrophotometer also includes a reflectance measurement area in the second light channel for selectively receiving a reflectance sample. When a sample is present, the light reflects off of the sample, the sample selectively absorbs certain wavelengths of light and reflects other wavelengths of light. When the spectrophotometer is in said transmittance mode, the transmittance sample is in the transmittance cell and a non-light altering element (such as a white tile) is in said reflectance measurement area. When the spectrophotometer is in the reflectance mode the transmittance cell is empty and the reflectance sample is received in the reflectance measurement area.

12 Claims, 7 Drawing Sheets

TRANSMITTANCE AND REFLECTANCE MEASURING SPECTROPHOTOMETER HAVING DUAL USE LIGHT CHANNELS

BACKGROUND OF THE INVENTION

1. Field of the Invention

This invention relates in general to a spectrophotometer capable of making reflectance or transmittance measurements. More particularly, the present invention relates to a spectrophotometer having input light channels which function as either reference or sample channels depending on whether the spectrophotometer is operating in reflectance or transmittance mode.

2. Discussion of the Related Art

In its simplest form, a spectrophotomter consists of a light source, a sample, and a detector, with a light filtering element either before or after the sample. When the filter is after the sample, then the detector could be a single element or an array of detectors such as a charge coupled device (CCD) or a photo diode array (PDA). A spectrophotometer can be used to determine color values of colored objects. The measurement can be either a reflectance measurement, where light is analyzed after it reflects off of a sample, or a transmittance measurement, where light, is analyzed after it passes through a solid or liquid sample. The sample in the transmittance mode absorbs certain wavelengths of light and allows other wavelengths to pass through the sample. The sample in the reflectance mode absorbs certain wavelengths of light and reflects the remaining wavelengths of light. The light from the sample passes through to the detector. In either mode, a separate channel of light, known as the reference channel, transmits unaltered directly to the detector. The color of the sample is determined through a comparison of the light from the reference channel to the light from the sample channel. Some spectrophotometers in the past could only measure color values in one of a reflectance or transmittance mode. In other spectrophotometers, one light channel is dedicated to reference measurement and the other light channel is dedicated to both reflectance and transmittance measurement. In a third type of spectrophotometer, three channels are provided. One light channel is a dedicated reference channel, one channel is dedicated to transmittance measurement and a third channel is dedicated to reflectance measurement. Each of these spectrophotometers of the past has problems associated therewith. It is desirable to have the ability to measure both reflectance and transmittance samples in one spectrophotometer. It is also desirable to have only two light channels to provide a compact unit.

In the spectrophotometer which has one channel which measures both reflectance and transmittance samples, a lower than necessary signal to noise ratio results from this arrangement. One such device is disclosed in U.S. Pat. No. 4,171,909, issued to Kramer et al., the disclosure of which is incorporated by reference. In this device, in the reflectance mode, the light in the measurement channel is reflected off of the sample, passes through the transmittance cell and optics associated therewith and is projected to the detector. In the transmittance mode, the light in the light measurement channel is reflected off of a non-light altering element (such as a white tile), and is projected through the transmittance sample and optics associated with the transmittance cell. Thus, in either mode the light in the sample channel is affected by unnecessary elements in the channel. In the transmittance mode, the sample light is affected by the non-light altering element, which has unintended and unavoidable effects on the light. In the reflectance mode, the light is affected by the transmittance cell optics. In either mode, an undesirable signal loss occurs. A spectrophotometer is needed which reduces this signal loss while preserving the ability to measure samples in both the reflectance and transmittance modes. A spectrophotometer is also needed which permits both transmittance and reflectance measurements using only two light channels.

SUMMARY OF THE INVENTION

A spectrophotometer is provided for selectively measuring color values of a transmittance sample in a transmittance mode and a reflectance sample in a reflectance mode. The spectrophotometer includes two light channels, a first light channel preferably from a light source to a first detector and a second light channel from the same light source to a second detector. The light channel conduct the light through the spectrophotometer and can be any type known in the art. Preferably, the light channels are optical fibers, although the light could be transmitted through the use of lenses and mirrors. Preferably, the light source is an incandescent lamp. It has been found that a high intensity tungsten lamp works well; however, a xenon or other bulb could also be used. With some light sources, it may be preferable to include a filter adjacent the light source to balance out wavelengths of light which are present in excessive amounts. With a tungsten bulb, a blue filter could be used to remove excess red wavelengths of light. Such light sources and filtering techniques are known in the art. The light channels include appropriate optical elements, such as a diffractive grating or prismatic member which disperses each of the light signals in a known manner. The light signals strike detectors and appropriate software (or circuitry) to compares the light striking the first and second detectors to determine the color value of a sample through spectral analysis. Thus, a comparison is made between light which has been altered by a sample and light from the light source which is unaltered. The circuitry to perform this comparison is known to those of ordinary skill in the art.

A transmittance cell is located in the first light channel for selectively receiving a transmittance sample. In the preferred embodiment, an optical fiber terminates at one end of the transmittance cell. Lenses are used at the ends of the optical fibers, as is known. A second optical fiber begins on the other end of the transmittance cell. Light from the first optical fiber passes through the transmittance cell and is picked up by the second optical fiber to be carried to the detector. As is known in the art, the transmittance sample could be a solid, such as a piece of colored glass or could be a liquid. Light passing through the transmittance sample is altered because the sample selectively absorbs some of the wavelengths of light and allows the remaining wavelengths of light to pass through the sample.

The spectrophotometer also includes a reflectance measurement area preferably including an illumination head in the second light channel for selectively receiving a reflectance sample. Preferably, several optical fibers deliver light to the reflectance measurement area. The illumination head is preferably hemispherical in shape and the optical fibers deliver light at angular locations around the sphere at a 45 degree angle to the sample to be measured. The illumination head has a black coating on its inner surface, as is known. Preferably, optical fibers are located at a fixed radial distance from the center of the illumination head. Light reflecting off of the sample enters an optical fiber at the center of the sphere and is conducted to the detector. When the light reflects off of the sample, the sample selectively absorbs certain wavelengths of light and reflects other wavelengths of light.

When the spectrophotometer is in the transmittance mode, the transmittance sample is in the transmittance cell and a non-light altering element is in the reflectance measurement area. Preferably, a white tile is used for the the non-light altering element. The light reflecting properties of the white tile are unaffected by time, temperature or humidity. When the spectrophotometer is in the reflectance mode, the transmittance cell is empty and the reflectance sample is received in the reflectance measurement area.

A method of measuring color values is also provided which selectively measures color values of a transmittance sample in a transmittance mode and a reflectance sample in a reflectance mode. Light is projected through a first light channel from a light source to a first detector. The first light channel has a transmittance cell in the channel. Light is projected through a second light channel from the light source to a second detector. The second light channel has a reflectance measurement area in the channel. A transmittance sample is placed in the transmittance cell and a non-light altering element is placed in the reflectance measurement area. The light striking the first and second detectors is then compared to determine the color value of the sample. To switch modes, the non-light altering element is removed from the reflectance measurement area and a reflectance sample is placed in the reflectance measurement area. The transmittance sample is removed from the transmittance cell. Light striking the first and second detectors is compared to determine color value of the sample.

With this method and apparatus only two light channels are required. With these two light channels, because the two channels have dual use, a better signal to noise ratio is obtained. Simple circuitry or software modifications are necessary to make use of this improvement, to reverse the meaning of sample and reference when required. In the past because the sample channel had both the reflectance measurement area and the transmittance cell in the channel, this resulted in an undesirable signal to noise ratio. By placing the reflectance measurement area in one channel and the transmittance cell in the other channel, a better signal to noise ratio is achieved. These and other details, advantages and benefits of the present invention will become apparent from the detailed description of the preferred embodiment hereinbelow.

BRIEF DESCRIPTION OF THE DRAWINGS

The preferred embodiment of the invention will now be described, by way of example only, with reference to the accompanying Figures wherein like members bear like reference numerals and wherein.

DETAILED DESCRIPTION OF A PREFERRED EMBODIMENT

Figure 1:
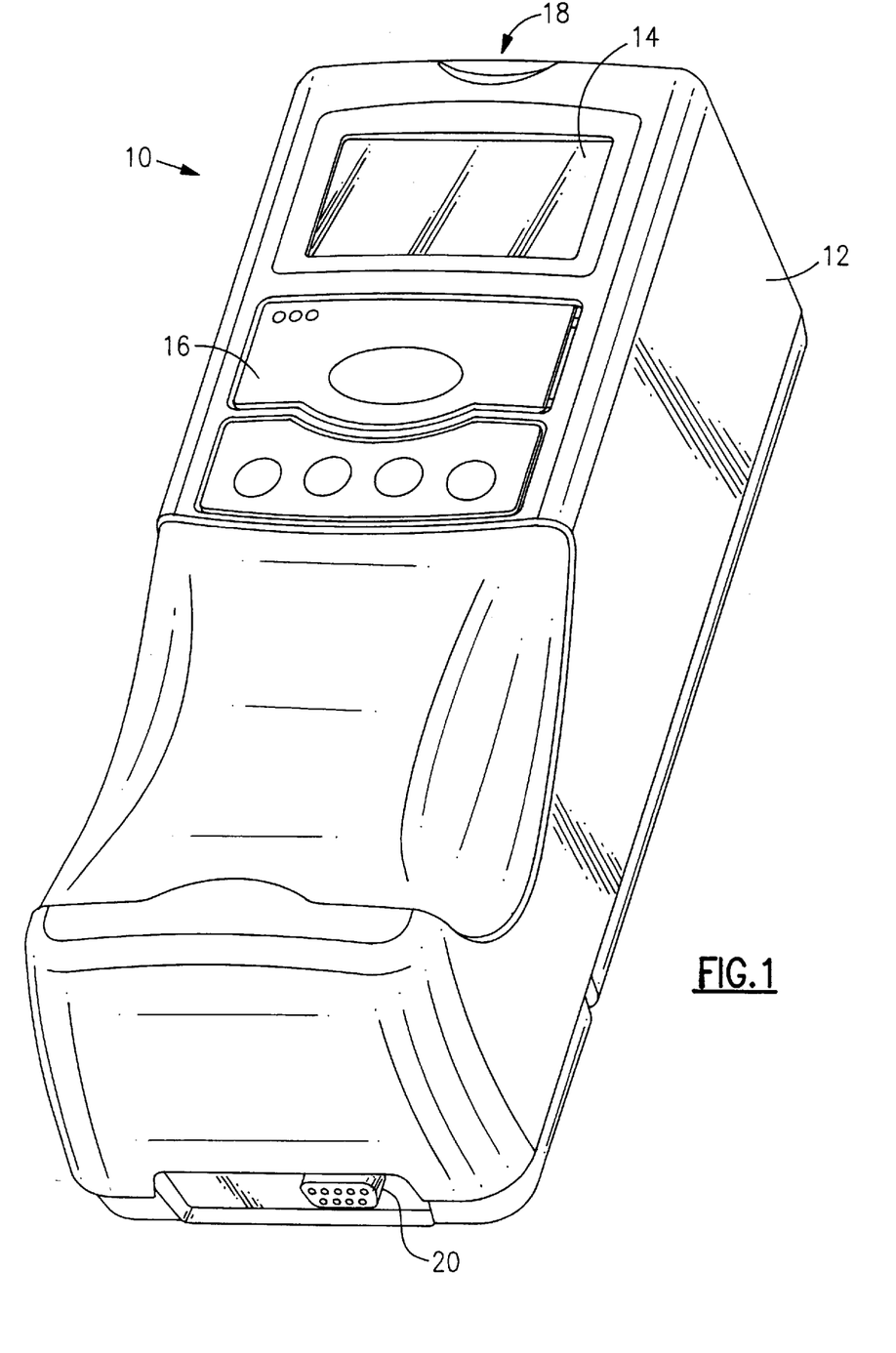
FIG. 1 is a perspective view f the spectrophotometer of the present invention.

Referring now to the drawings, which are for the purpose of illustrating the preferred embodiment of the invention and not for the purpose of limiting the same, FIGS. 1–10 show the present invention. FIG. 1 shows the spectrophotometer 10 of the present invention which can measure color values of samples through either transmittance measurement, where light passes through a sample or through reflectance measurement, where light reflects off of a sample. The spectrophotometer 10 includes a housing 12 having a display 14, preferably of the liquid crystal diode type; however, other types of displays are possible. The housing preferably has an access door 16 which can be opened such that a transmittance sample can be placed inside the spectrophotometer, as described below. The housing 12 also has an reflectance measurement area 18 (FIG. 3) which can accept a reflectance sample, also as described below. In the preferred embodiment, the reflectance measurement area 18 is in the form of a hemispherical illumination head 19 (FIG. 8), although other configurations of reflectance measurement areas 18 are possible and known to those of ordinary skill in the art. The spectrophotometer 10 also includes an electrical connector 20 adapted to transmit data from and receive power for the spectrophotometer 10.

Figure 2:
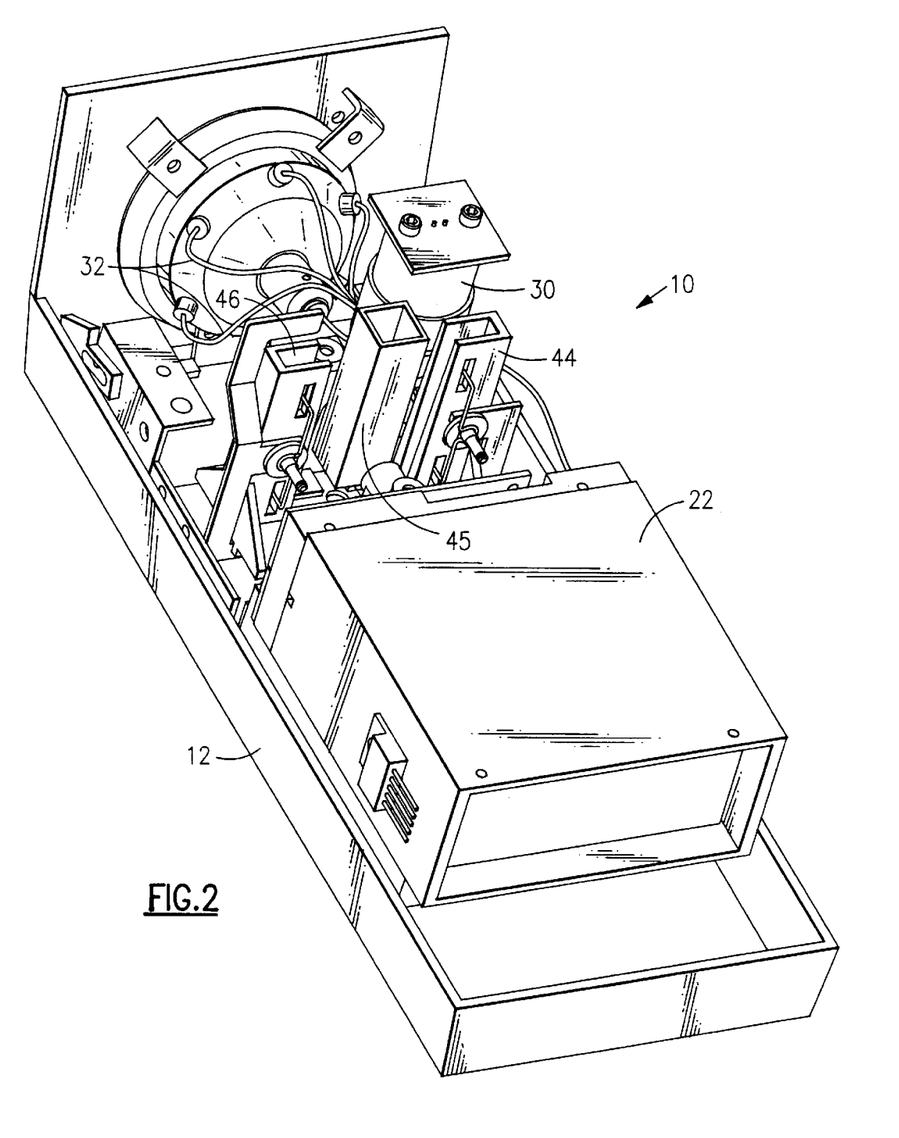
FIG. 2 is a perspective view of the spectrophotometer of FIG. 1 with the cover removed.
Figure 3:
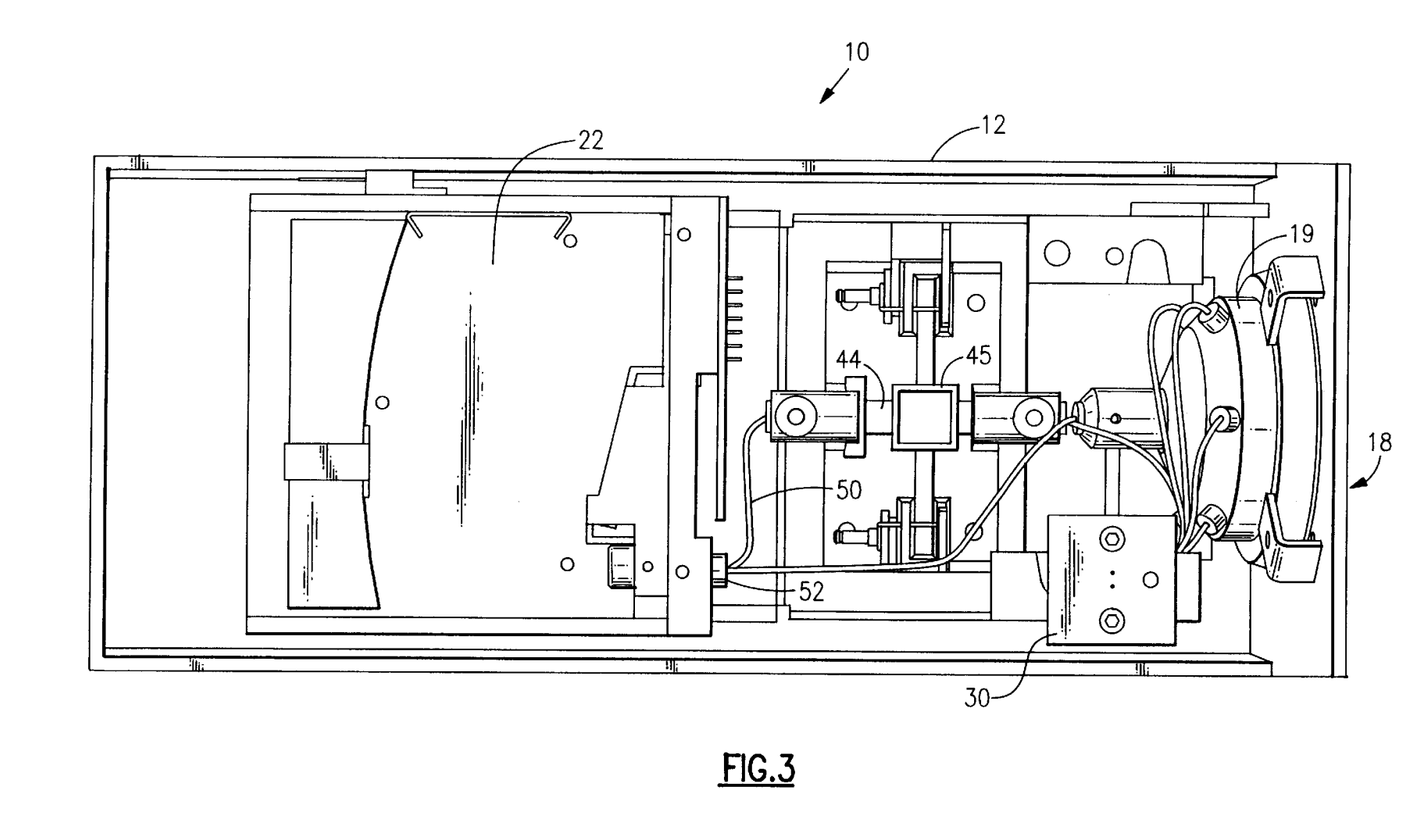
FIG. 3 is a top view of the spectrophotometer of FIG. 1.
Figure 4:
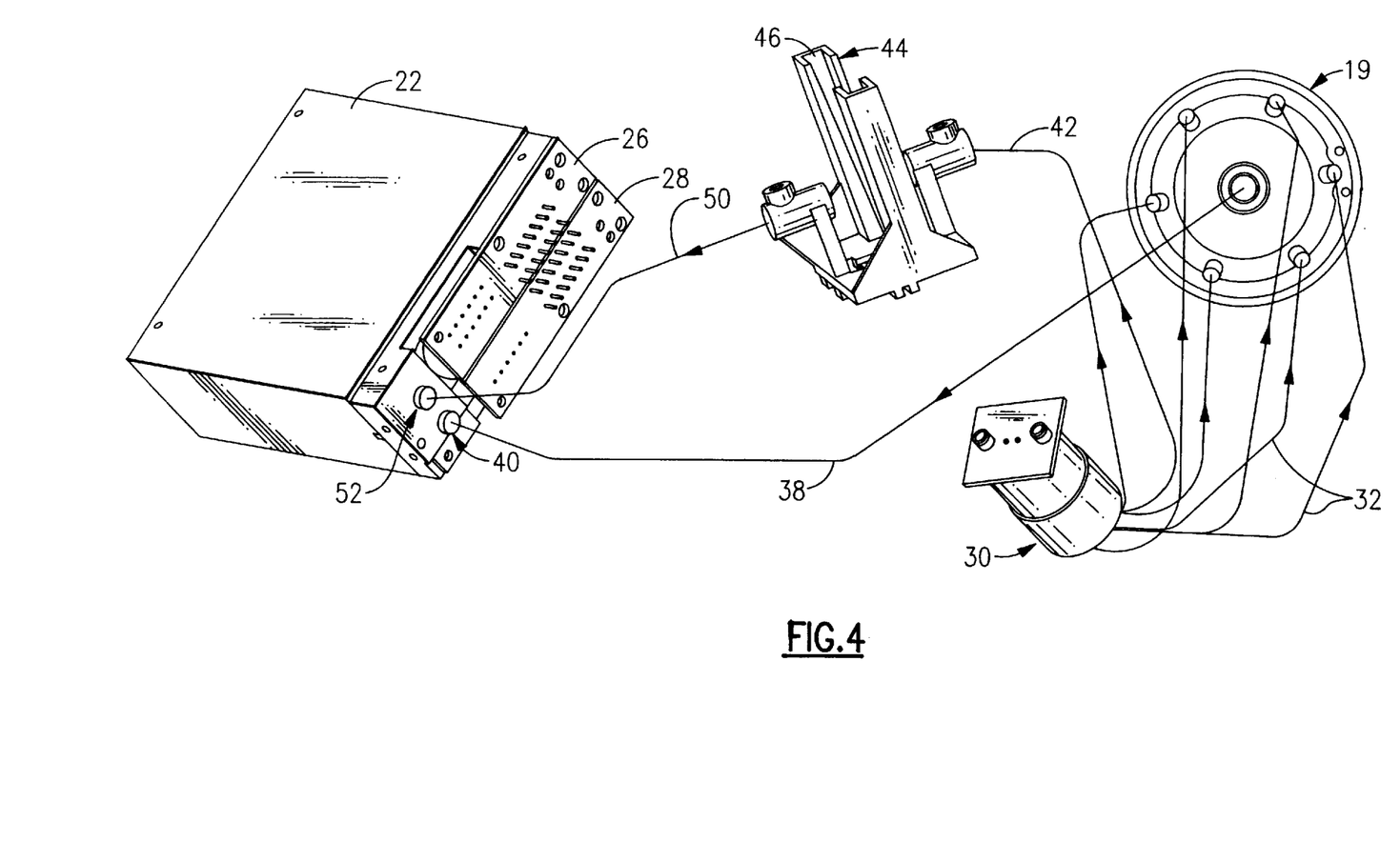
FIG. 4 is an exploded diagrammatic view of the spectrophotometer of the present invention showing the light channels.

Turning to FIG. 2, the spectrophotometer 10 includes a spectrograph 22 adapted to receive light from both the reflectance measurement area 18 and a transmittance cell 44 with a cuvette holder 45 for holding liquid samples. For solid samples the cuvette holder 45 is removed (FIGS. 4–6 and 9–10) The spectrograph 22 transmits the light, by means of mirrors and lenses (not shown) to detectors 26 and 28 (FIG. 4). The detectors 26 and 28 are photo diode arrays (PDA). Circuitry or software compares light striking the detectors 26 and 28. By comparing the light which is unchanged with light which has been changed by a sample, the spectrograph 22 determines the color of the sample.

Figure 5:
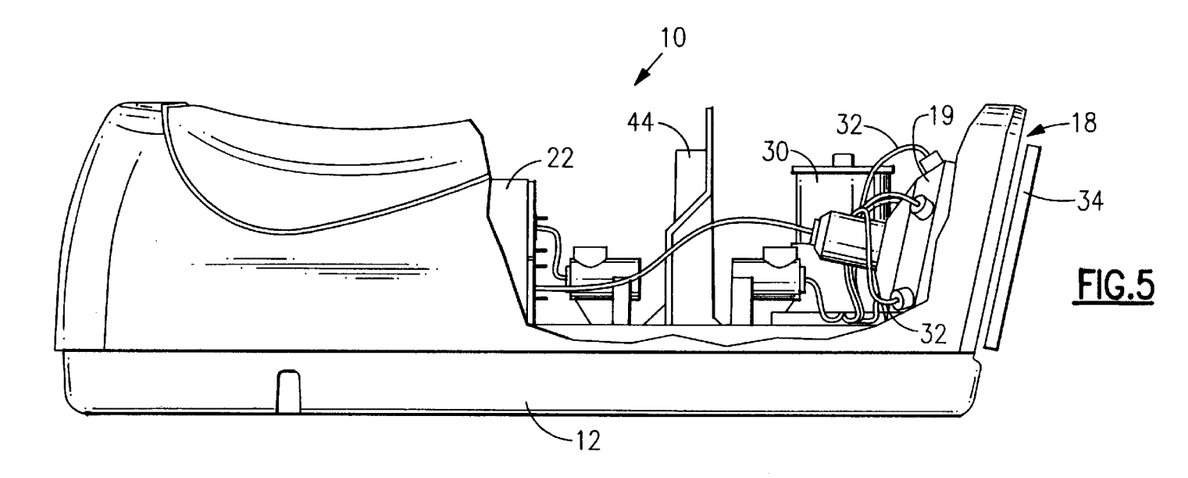
FIG. 5 is a side view of the spectrophotometer of FIG. 1 with the cover partially removed and with a reflectance sample.
Figure 9:
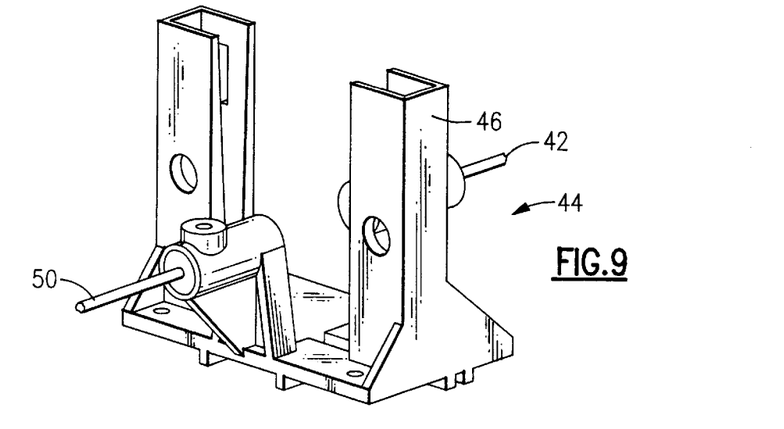
FIG. 9 is a perspective view of the transmittance cell of the present invention.
Figure 10:
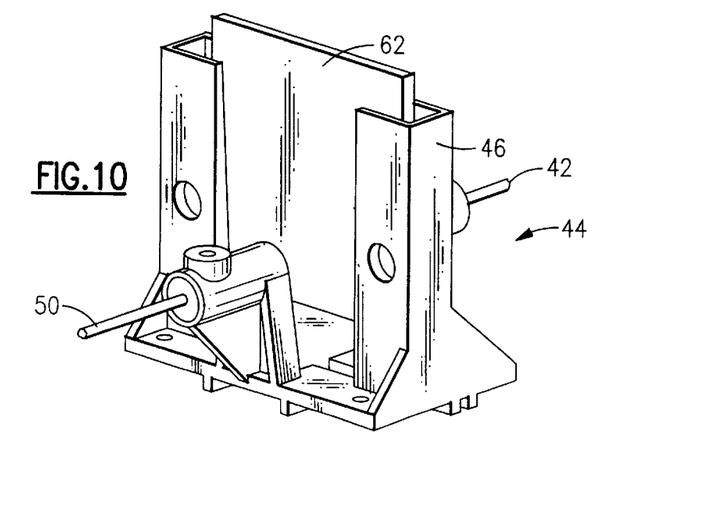
FIG. 10 is a perspective view of the transmittance cell of FIG. 9 with a transmittance sample in the transmittance cell.

Turning to FIGS. 3–8, the light source 30 is shown. The light source could be any suitable lamp. Preferably, an incandescent lamp (not shown) provides the light required by the spectrophotometer 10. Light from the light source 30 is carried by optical fibers 32 to the reflectance measurement area 18. Preferably a plurality of optical fibers 32 are disposed around the illumination head 19 and enter the illumination head 19 at a 45 degree angle to the vertical. As shown in FIG. 5, a sample 34 is placed in the reflectance measurement area 18. Light from the illumination head 19 strikes the sample 34 and is reflected into the center of the illumination head 36 ( FIG. 8). The light enters optical fiber 38 and is transmitted to a first light input 40. Light from the light source 30 is also transmitted through optical fibers 42 to a transmittance cell 44 (FIGS. 9 and 10). The transmittance cell 44 has a solid sample holder 46. Optical fiber 42 ends at transmittance cell 44. The light from optical fiber 42 is transmitted through the transmittance cell 44 and is picked up at optical fiber 50. The light is transmitted by optical fiber 50 to a second light input 52.

The operation of the spectrophotometer 10 of the present invention will now be described in connection with the two modes of operation. In the reflectance mode, a reflectance sample 34 is placed in the reflectance measurement area 18. In this reflectance measurement mode, the transmittance cell 44 remains empty. The light from the reflectance measurement area 18, after having been altered by the sample 34 is transmitted to the first light input 40. The light passing through the empty transmittance cell 44 is transmitted to the second light input 52 in an unaltered state. The light from the first light input 40 is transmitted to the detector 26. The light from the second light input is transmitted to the detector 28. The spectrograph compares the light striking the two detectors 26 and 28 and, based on the differences in the wavelength composition determines the color value of the sample. This color value is displayed in numerical form on the display 14, as is known in the art.

Figure 6:
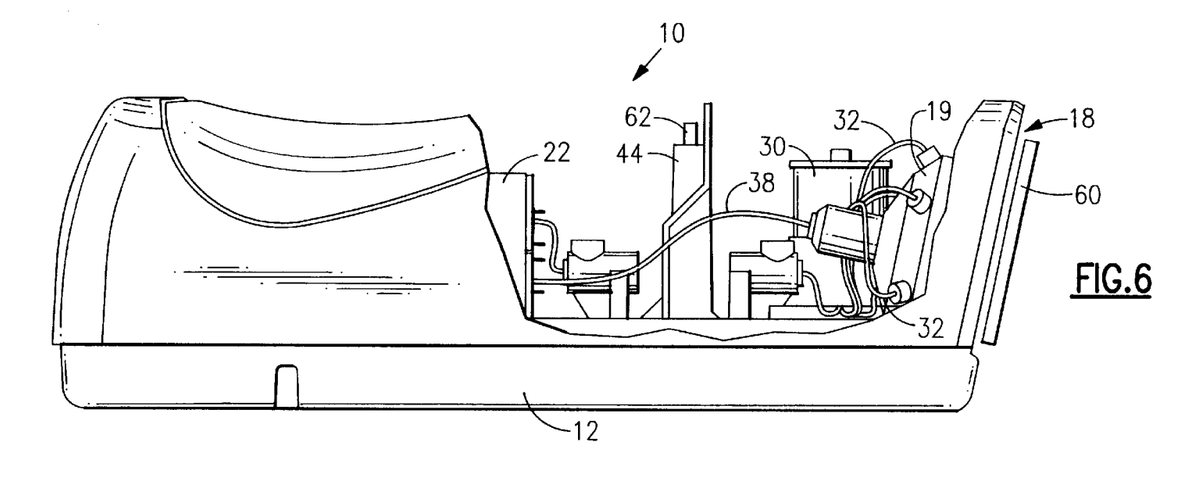
FIG. 6 is a side view of the spectrophotometer of FIG. 1 with the cover partially removed and with a non-light altering element.
Figure 7:
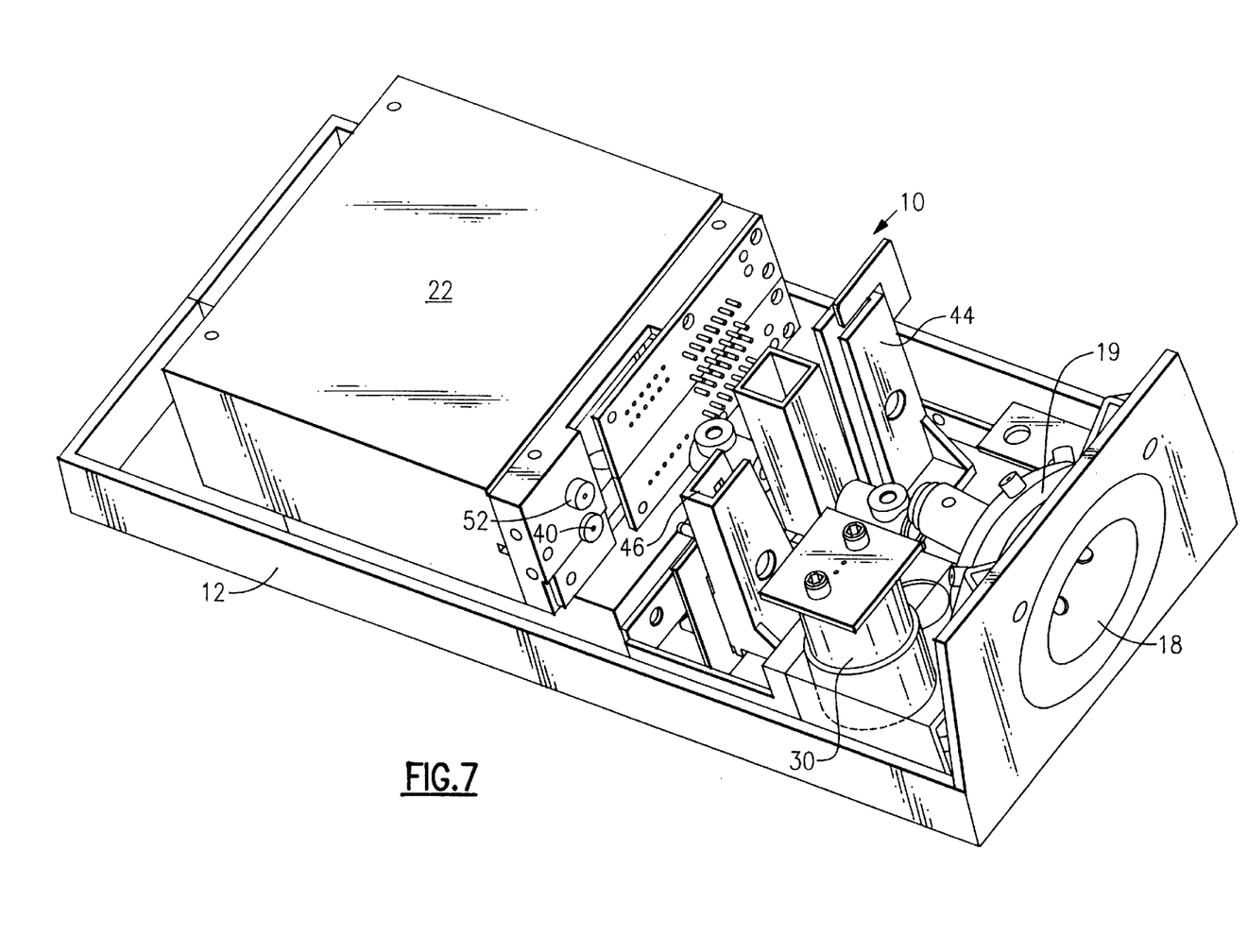
FIG. 7 is a perspective view of the spectrophotometer of FIG. 1.
Figure 8:
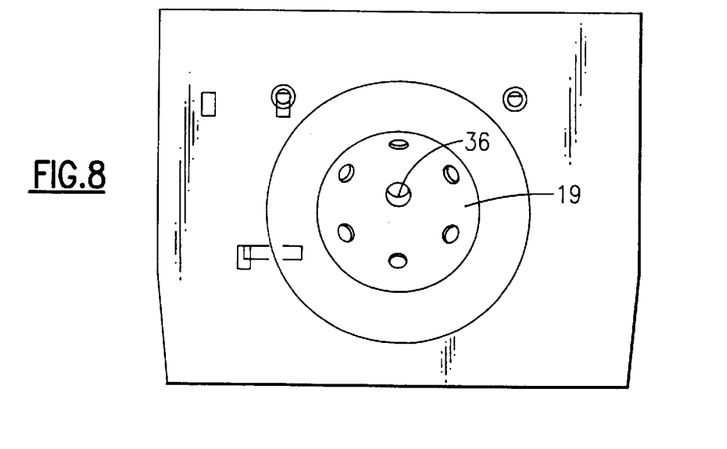
FIG. 8 is a front view of the spectrophotometer of FIG. 1 showing the illumination head.

In the transmittance mode, the reflectance sample 34 is replaced by a non-light altering element such as a white tile 60 (FIG. 6). In this transmittance measurement mode, a transmittance sample 62 is placed in the transmittance cell 44. The light from the reflectance measurement area 18, after reflecting off of the non-light altering element 60, is transmitted to the first light input 40 in an unaltered state. The light passing through the transmittance cell 44 is altered by the transmittance sample 62 and is transmitted to the second light input 52 in an altered state. The light from the first light input 40 is transmitted to the detector 26. The light from the second light input 52 is transmitted to the detector 28. The spectrograph compares the light striking the two detectors 26 and 28 and, based on the differences in the wavelength composition, determines the color value of the sample. This color value is displayed in numerical for on the display 14.

While this invention has been described in detail with reference to a preferred embodiment, it should be appreciated that the present invention is not limited to that precise embodiment. Rather, in view of the present disclosure which describes the best mode for practicing the invention, many modifications and variations would present themselves to those of skill in the art without departing from the scope and spirit of this invention, as defined in the following claims.

What is claimed is:

1. A method of selectively measuring color values of a transmittance sample in a transmittance mode and a reflectance sample in a reflectance mode, comprising the steps of:
   providing a first light channel from a light source to a first detector, the first light channel having a transmittance cell;
   providing a second light channel from said light source to a second detector, the second light channel having a reflectance measurement area;
   placing a transmittance sample in said transmittance cell and a non-light altering element in said reflectance measurement area;
   comparing light passing through said first and second light channels and striking said first and second detectors to determine the color value of the transmittance sample;
   removing said non-light altering element from said reflectance measurement area;
   inserting a reflectance sample in said reflectance measurement area;
   removing said transmittance sample from said transmittance cell;
   comparing light passing through said first and second light channels and striking said first and second detectors to determine color value of the sample.

2. A method of selectively measuring color values of a transmittance sample in a transmittance mode and a reflectance sample in a reflectance mode, comprising the steps of:
   providing a first light channel from a light source to a first detector, the first light channel having a transmittance cell;
   providing a second light channel from said light source to a second detector, the second light channel having a reflectance measurement area;
   inserting a reflectance sample in said reflectance measurement area;
   comparing light striking said first and second detectors to determine color value of the reflectance sample;
   removing said reflectance sample from said reflectance measurement area;
   placing a transmittance sample in said transmittance cell and a non-light altering element in said reflectance measurement area;
   comparing light striking said first and second detectors to determine the color value of the transmittance sample.

3. Apparatus for selectively measuring color values of a transmittance sample in a transmittance mode and a reflectance sample in a reflectance mode, comprising:
   a first detector;
   a first light channel from a light source to said first detector;
   a second detector;
   a second light channel from said light source to said second detector;
   means for determining color values by comparison between light striking said first and second detectors;
   a transmittance cell in said first light channel for selectively receiving said transmittance sample;
   a non-light altering element;
   a reflectance measurement area in said second light channel for selectively receiving said reflectance sample such that when said apparatus is in said transmittance mode, said transmittance sample is in said transmittance cell and said non-light altering element is in said reflectance measurement area and when said apparatus is in said reflectance mode said transmittance cell is empty and said reflectance sample is received in said reflectance measurement area.

4. The apparatus of claim 3 wherein said reflectance measurement area includes a hemispherical illumination head.

5. The apparatus of claim 4 wherein said second light channel includes a plurality of optical fibers.

6. The apparatus of claim 5 wherein said optical fibers transmit light to said illumination head and are disposed angularly around said illumination head.

7. The apparatus of claim 6 wherein said optical fibers are disposed angularly around said illumination head at a fixed radial distance from the center of said illumination head.

8. Apparatus for measuring color values of a sample by comparison between light in an unchanged condition and light which has been changed by the sample, comprising:
   a light source;
   first light detecting means for detecting light from said light source;
   second light detecting means for detecting light from the light source;
   a reflectance sample measurement area;
   a first light channel from said light source to said reflectance sample measurement area and extending from said reflectance sample measurement area to said first light detecting means;

a transmittance cell;

a second light channel from said light source, extending through said transmittance cell and to said second light detecting means, said apparatus being adapted to selectively measure color values in a reflectance mode and a transmittance mode, in said reflectance mode, the sample is placed adjacent said reflectance measurement area wherein light from said light source is altered by said sample and transmitted along said first light channel to said first light detecting means and light transmitted from said light source is projected along said second light channel to said second light detecting means and in said transmittance mode, a non-light altering element is adjacent in said reflectance measurement area, the sample is in said transmittance cell and light transmitted from said light source is projected along said second light channel through said transmittance cell where said light is altered by said sample and is projected along said second light channel to said second light detecting means and light from light source projecting along said first light channel transmitted to said reflectance sample measurement area is reflected off of said non-light altering element and is transmitted to said first light detecting means; and means for comparing light from said first and second light channels striking said first and second light detecting means to determine the color value of the sample.

9. The apparatus of claim 8 wherein said reflectance measurement area includes a hemispherical illumination head.

10. The apparatus of claim 9 wherein said second light channel includes a plurality of optical fibers.

11. The apparatus of claim 10 wherein said optical fibers transmit light to said illumination head and are disposed angularly around said illumination head.

12. The apparatus of claim 11 wherein said optical fibers are disposed angularly around said illumination head at a fixed radial distance from the center of said illumination head.

* * * * *